United States Patent [19]

Kawatani et al.

[11] Patent Number: 4,576,680
[45] Date of Patent: Mar. 18, 1986

[54] METHOD OF SIZING PAPER

[75] Inventors: Kimio Kawatani, Suita; Takashi Fujikawa, Kyoto; Eiji Watanabe, Osaka, all of Japan

[73] Assignees: Nippon Petrochemicals Co., Ltd.; Arakawa Kagaku Kogyo Kabushiki Kaisha, both of Tokyo, Japan

[21] Appl. No.: 577,081

[22] Filed: Feb. 6, 1984

[30] Foreign Application Priority Data

Feb. 7, 1983 [JP] Japan ................................. 58-18563

[51] Int. Cl.$^4$ ...................... C07D 307/60; D21H 3/08
[52] U.S. Cl. .................................. 162/158; 162/164.6; 162/168.1; 162/168.3; 162/174; 162/175; 549/255
[58] Field of Search ..................... 526/272; 549/255; 162/158, 164.6, 168.1, 168.3, 174, 175; 106/135, 213; 524/112

[56] References Cited

U.S. PATENT DOCUMENTS 3,102,064  8/1963  Wurzburg et al. .................. 549/255
3,968,005  7/1976  Wurzburg ........................... 162/158
4,302,283  11/1981  Blitzer et al. ...................... 162/158

FOREIGN PATENT DOCUMENTS 1411376  10/1975  United Kingdom ................ 549/255

Primary Examiner—Henry R. Jiles
Assistant Examiner—Bernard I. Dentz
Attorney, Agent, or Firm—Scully, Scott, Murphy & Presser

[57] ABSTRACT

An internal sizing agent for paper making which produces excellent sizing effect and which can be used in neutral to alkaline regions without the ordinarily employed fixing agent such as aluminum sulfate. The sizing agent contains a specific reaction product and/or hydrogenation product of said reaction product, said reaction product being prepared by adding maleic anhydride to branched internal olefins having 14 to 36 carbon atoms which branched internal olefins are obtained by oligomerizing one member or a mixture of two or more of olefins having 6 to 18 carbon atoms.

10 Claims, No Drawings

METHOD OF SIZING PAPER

BACKGROUND OF THE INVENTION (1) Field of the Invention

This invention relates to a paper sizing agent. More particularly, the invention relates to an internal paper sizing agent which is excellent in sizing effect and which can be employed in the range of neutral to alkali without using conventional fixing agents such as aluminum sulfate.

(2) Description of the Prior Art

In the paper manufacturing industry, the sizing agents that are prepared from natural rosins or modified rosins, especially fortified rosin sizing agents that are prepared by saponifying maleic-modified rosins, are regarded as most preferable ones and are widely used. These sizing agents are used together with aluminum sulfate and fixed to paper fibers in an acidic region of pH 4.0 to 5.0. Owing to the acidic condition with using these sizing agents, the following disadvantages are caused to occur. That is, paper making machinery suffers from corrosion, strength and durability of obtained paper are lowered, and inexpensive alkaline fillers such as calcium carbonate cannot be used because alkaline fillers are decomposed.

For this reason, neutral sizing agents which can be fixed to wood pulp without using aluminum sulfate, are proposed. For example, a sizing agent is known in which alkyl retene dimer is dispersed in water in the presence of cationic starch. This is, however, defective in that the cost is high and it takes much time to produce desired sizing effect.

Furthermore, several inventions have been proposed with regard to neutral sizing agents.

In U.S. Pat. No. 3,102,064, a sizing agent represented by the following general formula is disclosed.

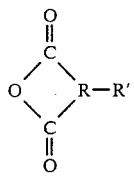

in which R represents a dimethylene or trimethylene radical and R' is a hydrophobic group containing more than 5 carbon atoms and is selected from the class consisting of alkyl, alkenyl, aralkyl, and aralkenyl groups.

Proposed in British Patent No. 2,015,612 are "substituted succinic anhydrides having substituent groups of butene oligomers having 16 to 40 carbon atoms". The compounds disclosed in both the above patent specifications are, however, unsatisfactory in sizing effect.

In U.S. Pat. No. 3,821,069, a reactive sizing agent is disclosed. The sizing agent is produced by reacting maleic anhydride and an internal olefin corresponding the following general structure:

$$R_x-CH_2-CH=CH-CH_2-R_y$$

and the reaction product is represented by the following general formula:

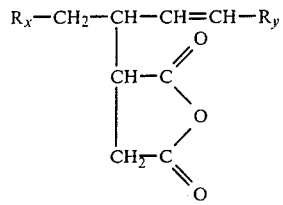

wherein $R_x$ and $R_y$ are, respectively, alkyl radicals containing at least 4 to 10 carbon atoms.

In Japanese Laid-Open Patent Publication No. 57-154,495 is proposed a reactive sizing agent which consists of an alkenyl succinic anhydride mixture that is produced by adding maleic anhydride to a mixture of straight chain internal olefins having 8 to 18 carbon atoms and double bonds which are almost evenly distributed to each position except α-position.

These sizing agents are high in reactivity with paper fiber and produce good sizing effect. However, they are liable to be hydrolyzed and they must be used as soon as possible after being emulsified. In addition, as the sizing effect varies widely, constant and uniform sizing effect cannot be expected in paper sizing operation.

BRIEF SUMMARY OF THE INVENTION

In order to eliminate the above defects in the conventional art, the inventors have earnestly made investigation and, as a result, the present invention has been accomplished.

It is, therefore, the primary object of the present invention to provide a novel paper sizing agent that is free from disadvantages caused to occur in the conventional paper sizing agents.

Another object of the present invention is to provide a paper sizing agent which produces good sizing effect and which is prepared without difficulty.

A further object of the invention is to provide a paper sizing agent which produces excellent sizing effect in neutral to alkaline conditions without using a fixing agent such as aluminum sulfate.

Still a further object of the present invention is to provide a paper sizing agent which is dispersed well in water, is compatible with various kinds of paper making additives, and is preserved for a long time.

According to the present invention, the paper sizing agent contains a reaction product and/or a hydrogenation product of said reaction product, wherein said reaction product is prepared by adding maleic anhydride to branched internal olefins having 14 to 36 carbon atoms which are obtained by oligomerizing one member or a mixture of two or more of olefins having 6 to 18 carbon atoms.

DETAILED DESCRIPTION OF THE INVENTION

The present invention will be described in more detail.

The olefins used as starting materials for preparing the paper sizing agent of this invention are those having 6 to 18 carbon atoms, preferably 8 to 12 carbon atoms. If they can be oligomerized, olefins of any type can be employed.

The reaction product that are made from olefins having 5 or less carbon atoms, is deficient in sizing effect and preservability. Meanwhile, in the case that the number of carbon atoms of starting olefin exceeds 18, the obtained reaction product can produce sizing effect but it becomes too viscous, which is inconvenient for practical uses.

Preferable starting materials are exemplified by straight chain α-olefins such as octene-1, decene-1 and dodecene-1; straight chain internal olefins such as octene-2, octene-4, decene-3, decene-5, undecene-3, undecene-5, dodecene-4, dodecene-6, tetradecene-5 and tetradecene-7; and branched internal olefins such as diisobutylene and propylene trimer.

These olefins can be used either singly or in a mixture of two kinds or more. From economical viewpoint, mixtures of two or more kinds of olefins are preferably used. The branched internal olefin having 14 to 36 carbon atoms can be obtained by treating the above olefins under proper conditions in the presence of an oligomerization catalyst.

As the oligomerization catalysts, acid catalysts and organometallic complexes are used. Acid catalysts are exemplified by homogeneous or heterogeneous catalysts such as cation exchange resin having fluorosulfonic groups, fluoromethane sulfonic acid, $AlCl_3$-electron donor, $BF_3$-electron donor, mineral acids such as $H_2SO_4$, acid clay minerals such as acid clay and activated clay, synthetic silica-alumina and heteropolyacids.

Exemplified as the organometallic complex catalysts are $Al_2(C_2H_5)_3Cl_3$-$TiCl_4$, $Al_2(C_2H_5)_3Cl_3$-$VOCl_3$, $AlC_2H_5Cl_2$-$\pi$-$C_3H_5NiBr$, $Al_2(C_2H_5)_3Cl_3$-$Ni(C_5H_7O_2)_2$, $Al(C_2H_5)_2Cl$-$Cr(C_5H_7O_2)_3$, and $Cl_2Pd(PhCN)_2$.

The treatment of oligomerization can be done under the conditions of temperatures from 30° to 300° C., pressures from the atmospheric pressure to 30 Kg/cm², and reaction times from 1 to 30 hours. These conditions may be selected according to the kind of starting material of olefin and catalyst employed.

Any type of treatment system such as batchwise, semi-batchwise or continuous operation can be adopted. In the case of continuous operation, LHSV (liquid hourly space velocity) is preferably in the range of 0.1 to 20.

When olefins are treated in the presence of the foregoing catalysts, either only olefins or olefins together with an inert solvent can be used.

When olefins are oligomerized by the above catalyst treatment, oligomers having 14 to 36 carbon atoms are obtained, while heavier components are sometimes produced. In that case, in order to eliminate substantially the heavier components, the branched internal olefin of this invention must be separated by distillation.

The branched internal olefin that is prepared through the above-described procedure, has a double bond at 3-position or a higher position of main carbon chain, and it contains 50% or more of components which have an alkyl branch or branches on one or both the carbon atoms of the double bond. (The branched internal olefin having one alkyl branch joined to only one carbon atom of double bond is hereinafter referred to as "tri-substituted olefin" and the one having two alkyl branches respectively joined to both the carbon atoms of double bond is referred to as "tetra-substituted olefin".)

The tri-substituted olefin is exemplified by 7,8-dimethyltetradecene-6; 2,2,4,6,6,8,8-heptamethylnonene-4; 2,2,4,6,6,8,8-heptamethylnonene-3; and 2,4,9,11-tetramethyl5-ethyldodecene-5.

The tetra-substituted olefin is exemplified by 6,7-dimethyldodecene-6; 5-ethyl-6-methylundecene-5; 5,6-diethyldecene-5; 4-propyl-5-ethylnonene-4; 7,8-dimethyltetradecene-7; 6-ethyl-7-methyltridecene-6; 6,7-diethyldodecene-6; 5-propyl-6-ethylundecene-5; 9,10-dimethyloctadecene-9; 8-ethyl-9-methylheptadecene-8; 6-butyl-7-ethyltetradecene-6; 6-butyl-7-methylpentadecene-6; 11,12-dimethyldocosene-11; 10-ethyl-11-methylheneicosene-10; 9-propyl-10-methyleicosene-9; 8-butyl-9-ethyloctadecene-8; 13,14-dimethylhexacosene-13; 12-ethyl-13-methylpentacosene-12; 12,13-diethyltetracosene-12; 10-butyl-11-ethyldocosene-10; 10-butyl-11-propylheneicosene-10; and 2,4,6,7,9,11-hexamethyldodecene-6.

As a paper sizing agent, more preferable range of the number of carbon atoms is 16 to 28, and it is desirable that the branched internal olefin contains a dimer of olefin starting material or components derived from the dimer.

The sizing agent obtained from the oligomer having less than 14 carbon atoms cannot produce satisfactory sizing effect and its preservability is not good enough. With the sizing agent obtained from the oligomer having more than 36 carbon atoms, the viscosity of the sizing agent becomes too high, which is undesirable for practical uses because the use of the sizing agent is not easy.

The branched internal olefin of this invention is different from the olefins that are disclosed in the foregoing prior art references.

That is, in U.S. Pat. No. 3,102,064, iso-octadecenyl, n-hexadecenyl, dodecenyl, dodecyl, decenyl, octenyl, nonenyl, and triisobutenyl groups are disclosed as the alkyl or alkenyl groups of alkyl or alkenylsuccinic anhydrides. However, these are derived from linear olefins or triisobutylene and they are different from the branched internal olefin of the present invention.

In British Patent No. 2,015,612, the employed olefin is the oligomer of butene, $C_4$-olefin. This oligomer is different from the branched internal olefin that is the oligomer obtained from olefins having 6 to 18 carbon atoms.

In U.S. Pat. No. 3,821,069, internal olefins represented by the general formula:

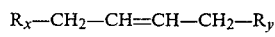

$$R_x-CH_2-CH=CH-CH_2-R_y$$

such as octadecene-9, tetradecene-7, hexadecene-7 and eicodecene-11 are disclosed. These olefins are linear olefins and any carbon atom of double bond has no alkyl branch. Furthermore, it is considered that they are not the products that are obtained by oligomerization of olefins having 6 to 18 carbon atoms. Accordingly, they are different from the branched internal olefin of this invention.

The olefins disclosed in Japanese Laid-Open Patent Publication No. 57-154,495 are linear olefins, which are apparently different from the branched internal olefin of this invention.

According to the present invention, excellent paper sizing agent can be obtained because the specific branched internal olefin that is different from the conventional art, is used.

The addition reaction between maleic anhydride and the branched internal olefin that is prepared by the above-described process, is carried out in accordance with the conventional method. That is, both the materials are heated in an inert gas atmosphere such as nitrogen gas at temperatures of 180° to 250° C. and at atmospheric pressure or at an elevated pressure. This reaction proceeds easily. The molar ratio of both the materials is not restricted, however, 0.2 to 2 moles of maleic anhydride is generally used to 1 mole of the branched internal olefin. After the reaction, alkenylsuccinic anhydride as the reaction product is obtained by removing unreacted maleic anhydride and the branched internal olefin by means of reduced pressure distillation.

In this addition reaction, the main reaction product is an adduct of 1 mole of the branched internal olefin with 1 mole of maleic anhydride. However, small quantities of by-products such as an adduct of 1 mole of the olefin with 2 moles of maleic anhydride, 1:2-adduct, and polymer of maleic anhydride, are produced. These by-products may be either removed or not removed. From economical viewpoint, it is desirable to use the reaction product without removing the by-products. The reaction product is further subjected to ordinary hydrogenation reaction with using a solid catalyst such as palladium or Raney nickel to obtain alkylsuccinic anhydride, which comes also within the scope of this invention.

In the addition reaction with maleic anhydride, reactivity hardly varies with the kind of olefin component of of the branched internal olefin. Therefore, tri-substituted olefins and tetra-substituted olefins as the main components of the branched internal olefins are effectually converted into adducts with maleic anhydride, and they fulfill excellent function as the main components of a sizing agent.

Sizing is carried out by using the reaction product, i.e. sizing agent, that is obtained by the above-described procedure. When the sizing agent is used, it is homogeneously dispersed in water by a forced mixing apparatus such as a homogeneous mixer, homogenizer and high pressure emulsifier and the obtained dispersion is added to pulp slurry.

When the sizing agent is dispersed in water, a protective colloid or dispersing agent such as cationized starch, gelatin, polyvinyl alcohol, cationic polyacrylamide, or polyethylene imine, or a nonionic emulsifier can be used together. In the above emulsifiers, the cationic starch, cationic polyacrylamide and polyethylene imine have also the effect as a fixing agent to pulp.

The nonionic emulsifiers are exemplified by polyoxyethylene alkyl ether, polyoxyethylene alkyl ester, polyoxyethylene sorbitan fatty acid ester, polyoxyethylene alkylphenol, polyoxyethylene alkylamine, polyoxyethylene alkylamide, ester of polyalcohol and fatty acid, and higher alcohol.

In the present invention, the quantity of the foregoing protective colloid used together with the paper sizing agent, is determined according to the dispersibility in water and fixing property to pulp of the paper sizing agent. The quantity of the protective colloid is generally in the range of 50 to 500%, preferably 100 to 200% relative to a sizing agent.

The quantity of nonionic emulsifier is determined according to the dispersibility of paper sizing agent, which is generally in the range of 3 to 30%, preferably 5 to 20%.

In the case that the above nonionic emulsifier is previously mixed into the paper sizing agent of the present invention and the mixture is dispersed in water, any forced mixing apparatus is not necessary, which apparatus is used when dispersing is done with using a protective colloid. The sizing agent with nonionic emulsifier can be easily dispersed only by using a pulp-mixing aspirator or by passing the mixture through an orifice (this method is hereinafter referred to as "self-emulsifying method"), which method can simplify the paper making process.

As described above, the nonionic emulsifying agent is effective in producing self-emulsifying property. However, when the paper sizing agent of this invention is mixed with polyoxyethylene sorbitan fatty acid ester, polyoxyethylene alkyl ether, polyoxyethylene alkylphenol or polyoxyethylene alkyl ester that gives good self-emulsifying property, and the mixture is left standing still, the dispersing property in water of the mixture becomes worse with the lapse of time. The sizing effect becomes worse accordingly, which is not desirable for practical uses.

However, the inventors have found that, when a specific emulsifying agent that is prepared by acetylating the terminal hydroxyl group of nonionic emulsifying agent with acetic anhydride, is mixed with the paper sizing agent of this invention, the above-mentioned stability and dispersibility in water become good. That is, the above specific emulsifying agents are acetylated products which correspond to polyoxyethylene sorbitan fatty acid ester, polyoxyethylene alkyl ether, polyoxyethylene alkylphenol and polyoxyethylene alkyl ester.

Incidentally, the acetylated product of polyoxyethylene fatty acid ester is obtained by the following method. Sorbitan is a mixture of intramolecular dehydration products of sorbitol such as one-mole dehydration products of 1,4-sorbitan, 3,6-sorbitan and 1,5-sorbitan, and two-mole dehydration product of 1,4,3,6-sorbide. The sorbitan is esterified with a fatty acid to obtain the sorbitan fatty acid ester. Ethylene oxide is then added to the sorbitan fatty acid ester and terminal hydroxyl groups of the reaction product are acetylated by acetic anhydride, thereby obtaining the above acetylated product.

The mixing quantity of the acetylated emulsifying agent to the sizing agent of the invention, is generally 3 to 30%, preferably 5 to 20% by weight.

The quantity of paper sizing agent used in the present invention varies to some degree according to the kind and uses of paper to be produced. The quantity is, however, generally in the range of 0.05 to 5.0% by weight to dry-basis pulp. It is possible to add more than 5.0 weight percent of paper sizing agent but the increase of sizing effect can hardly be expected so that the addition of more than 5% is not advantageous in economical viewpoint.

As described above, when the sizing agent of this invention is used together with a cationic protective colloid or an nonionic emulsifying agent in neutral or alkaline region, the sizing agent can be dispersed in water. Owing to the use of specific olefin oligomers which are different from the conventional art, the sizing agent produces excellent sizing effect, that is, desired sizing effect can be obtained by using smaller quantity of the sizing agent as compared with the conventional art. Furthermore, it maintains good sizing effect during long term preservation, that is, the sizing effect of sizing medium after long term preservation is almost the same as the effect produced just after it is made up. This fact is advantageous as compared with conventional sizing agents. Still further, when the sizing agent of the present invention is used by mixing with a specific acetylated emulsifying agent, more excellent characteristics in self-emulsifying property and preservability are produced, with which the simplifying of paper making process can be expected.

The paper sizing agent of this invention can be used singly, of course, and if desired, it can be used together with known sizing agents by mixing with them in any mixing ratio.

It should be noted also that known pigments and fillers such as clay, talc, titanium oxide, calcium carbonate, calcium sulfate and diatomaceous earth can be added to paper material that has been sized with the sizing agent of the present invention.

The preparation and uses of the sizing agent of the invention will be described in more detail in the following examples. It should be noted, however, that the present invention be limited not by the specific disclosure herein but only by the appended claims.

EXAMPLE 1

A 1 liter glass-made reaction vessel equipped with a stirrer, thermometer and cooling pipe, was fed with 500 ml of n-octene-1 and 50 g of Nafion 511 (trademark of cation exchange resin containing fluorosulfonic radical, made by E. I. du Pont de Nemours). Reaction was carried out for 1 hour at 120° to 140° C. After the reaction, Nafion 511 was separated from the reation mixture by filtration and the reaction mixture was treated by an adsorbent, Kyowaad 500 (trademark, made by Kyowa Chemical Industry Co., Ltd., $Mg_6Al_2(OH)_{16}CO_3.4H_2O$) to eliminate the free acid derived from the catalyst. After that, by reduced pressure distillation, 225 g of branched internal olefin having 16 or more carbon atoms was obtained. The distribution of carbon atom numbers was $C_{16}$: 89%, $C_{24}$: 11%. According to NMR analysis and IR analysis, the branched internal olefin contained 65% of tri-substituted olefin and tetra-substituted olefin.

A stainless steel autoclave equipped with a stirrer and a thermometer was fed with 150 g of the branched internal olefin and 65 g of maleic anhydride. The air in the reaction system was completely replaced by dry nitrogen gas and reaction was carried out for 4 hours at 210° C.

The reaction mixture was then subjected to reduced pressure distillation to remove unreacted olefin and maleic anhydride and 101 g of maleic modified reaction product was obtained. The viscosity of the reaction product was 510 cp (at 25° C.) and acid value was 316.

According to NMR analysis and IR analysis, the unreacted olefin contained 62% of tri-substituted olefin and tetra-substituted olefin and the distribution of types of double bonds after the maleic modification was almost the same as the distribution before the reaction.

EXAMPLE 2

A 1 liter glass-made reaction vessel equipped with a stirrer, thermometer and cooling pipe, was fed with 500 ml of n-dodecene-1 and 50 g of synthetic silica-alumina and the contents were allowed to react for 1 hour at 150° to 180° C. After the reaction, the catalyst was removed from the reaction mixture by filtration. By reduced pressure distillation, 163 g of dimer as the branched internal olefin was obtained from the reaction mixture. The branched internal olefin contained 56% of tri-substituted olefin and tetra-substituted olefin.

A stainless steel autoclave equipped with a stirrer and a thermometer was fed with 140 g of the branched internal olefin and 40.8 g of maleic anhydride. The air in the reaction system was completely replaced by dry nitrogen gas and reaction was carried out for 4 hours at 210° C. The reaction mixture was then subjected to reduced pressure distillation to remove unreacted olefin and maleic anhydride and 38 g of maleic modified reaction product was obtained. The viscosity of the reaction product was 893 cp (at 25° C.) and acid value was 260.1.

According to NMR analysis and IR analysis, the unreacted olefin contained 58% of tri-substituted olefin and tetra-substituted olefin and the distribution of types of double bonds after the maleic modification was almost the same as the distribution before the reaction.

EXAMPLE 3

A 2 liter glass-made reaction vessel equipped with a stirrer, thermometer and cooling pipe, was fed with 1 liter of octene-1, 150 ml of octane, 50 mmol of $Al_2(C_2H_{53})Cl_3$, 100 mmol of $TiCl_4$ and 30 mmol of diethylene glycol diethyl ether and the contents were allowed to react for 10 hours at 30° C. After the reaction, 50 ml of methanol was added to deactivate the catalysts and the reaction mixture was rinsed with HCl aqueous solution and then with water. The conversion ratio of octene-1 was 63% and the quantities of dimer, trimer, and tetramer and higher oligomers were 19.8%, 8.5%, and 71.7%, respectively. By reduced pressure distillation of the reaction product, 108 g of dimer was obtained. The dimer contained 53% of tri-substituted olefin and tetra-substituted olefin.

A stainless steel autoclave equipped with a stirrer and a thermometer was fed with 100 g of the dimer and 43 g of maleic anhydride. The air in the reaction system was completely replaced by dry nitrogen gas and reaction was carried out for 4 hours at 210° C. After the reaction, unreacted olefin and maleic anhydride were removed from the reaction mixture and 58 g of maleic modified reaction product was obtained.

The viscosity of the reaction product was 533 cp (at 25° C.) and acid value was 352.9. The unreacted olefin contained 55% of tri-substituted olefin and tetra-substituted olefin. The distribution of types of double bonds after the maleic modification was almost the same as the distribution before the reaction.

EXAMPLE 4

A stainless steel reaction vessel was filled with 30 ml of catalyst $Pt.Li_2O.Al_2O_3$. n-Paraffin mixture ($C_{10}$: 30%, $C_{11}$: 35%, $C_{12}$: 35%) was fed together with hydrogen gas to the reaction vessel at a temperature of 470° C., flow rate of 15 ml/min. and molar ratio of $H_2$/n-decane=8.0 to perform dehydrogenation. The olefin content in the effluent of the reaction vessel was about 10%. After the reaction, the reaction mixture was passed through molecular sieve and a mixture of straight chain internal olefins of $C_{10}$, $C_{11}$ and $C_{12}$ was obtained.

A stailess steel continuous reaction tube was filled with 100 ml of synthetic silica-alumina and it was maintained at 180° C. The above straight chain internal olefin was fed to the reaction tube at a flow rate of 100 ml/hour. The composition of the effluent of the reaction tube was monomer: 45%, dimer component: 46% and heavier components of trimer and higher oligomers: 9%. This reaction mixture was subjected to reduced pressure distillation to obtain branched internal olefin comprising dimer components.

The branched internal olefin (250 g) was reacted with 87 g of maleic anhydride in the like manner as Example 1 to obtain 102 g of maleic modified reaction product. The viscosity of the reaction product was 603 cp (at 25° C.) and acid value was 278. The content of tri-substituted olefin and tetra-substituted olefin in the branched internal olefin before the maleic modification was 72% and the value after the reaction was 75%, which values were almost the same.

EXAMPLE 5

A 1 liter glass-made reaction vessel equipped with a stirrer, thermometer and cooling pipe, was fed with 500 g of n-octene-1 and the vessel was maintained at temperatures between 120° and 130° C. Reaction was carried out for 2 hours with adding dropwise 17 ml of boron trifluoride-diethyl ether complex. After the reaction, remaining catalyst was neutralized and removed by adding 500 ml of 5% aqueous ammonia to the reaction mixture. The reaction mixture was then rinsed three times with 500 ml of water and the reaction mixture was desiccated by a desiccant. Then, 228 g of branched internal olefin having 16 to 32 carbon atoms was obtained by reduced pressure distillation of the above reaction mixture. The branched internal olefin contained 62% of tri-substituted olefin and tetra-substituted olefin.

A stainless steel autoclave equipped with a stirrer and a thermometer was fed with 100 g of the branched internal olefin and 50 g of maleic anhydride. The air in the reaction system was completely replaced by dry nitrogen gas and reaction was carried out for 24 hours at 190° C. The reaction mixture was then subjected to reduced pressure distillation to remove unreacted olefin and maleic anhydride and 43 g of maleic modified reaction product was obtained.

The viscosity of the reaction product was 321 cp (at 25° C.) and acid value was 338. The distribution of the types of double bonds in the unreacted olefin was the same as that in the olefin starting material.

EXAMPLE 6

Propylene was oligomerized with using polyphosphoric acid to obtain nonene (trimer of propylene). 500 g of the nonene was fed to 1 liter glass-made reaction vessel equipped with a stirrer, thermometer and cooling pipe and the reaction vessel was maintained at 100° C. This was allowed to react for 5 hours with adding dropwise 10 ml of trifluoromethane sulfonic acid. In the like manner as Example 5, the reaction mixture was then treated to obtain 156 g of dimer component as the branched internal olefin. This branched internal olefin contained tri-substituted olefin and tetra-substituted olefin as the main components.

An autoclave equipped with a stirrer and a thermometer was fed with 100 g of this branched internal olefin and 45 g of maleic anhydride. The air in the reaction system was completely replaced by dry nitrogen gas and reaction was carried out for 24 hours at 200° C.

After the reaction, 42 g of maleic modified reaction product was obtained by an ordinary method. The viscosity of the reaction product was 7300 cp (25° C.) and acid value was 299. The distribution of types of double bonds of the dimer was not varied during the reaction with maleic anhydride.

EXAMPLE 7

A 1 liter glass-made reaction vessel equipped with a stirrer, thermometer and cooling pipe was fed with 500 g of diisobutylene and the reaction vessel was maintained at 25° C. With adding dropwise 1 ml of trifluoromethane sulfonic acid, reaction was carried out for 5 hours. The obtained reaction mixture was treated in the like manner as Example 5 and 260 g of dimer component as the branched internal olefin was obtained. This branched internal olefin contained tri-substituted olefin and tetra-substituted olefin as the main components.

An autoclave equipped with a stirrer and a thermometer was fed with 100 g of the thus obtained dimer and 44 g of maleic anhydride. The air in the reaction system was completely replaced by dry nitrogen gas and reaction was carried out for 24 hours at 210° C. to obtain 57 g of maleic modified reaction product.

The viscosity of the reaction product was 13,000 cp (at 25° C.) and acid value was 378. The distribution of types of double bonds in the dimer was not varied during the reaction with maleic anhydride.

COMPARATIVE EXAMPLE 1

In the like manner as Example 1, n-pentene-1 was treated to obtain a maleic modified reaction product. The viscosity of the reaction product was 260 cp (at 25° C.) and acid value was 395.

COMPARATIVE EXAMPLE 2

In the like manner as Example 4, n-paraffin having 15 to 18 carbon atoms was treated to obtain n-olefin ($C_{15}$: 5%, $C_{16}$: 37%, $C_{17}$: 38%, $C_{18}$: 20%). Maleic anhydride was added to the n-olefin to obtain a maleic modified reaction product.

COMPARATIVE EXAMPLE 3

According to an ordinary method, 115 g of maleic anhydride was added to 300 g of n-octadecene-9 to obtain 248 g of maleic modified reaction product.

COMPARATIVE EXAMPLE 4

An oligomer having 15 to 18 carbon atoms ($C_{15}$: 63%, $C_{16}$: 13%, $C_{17}$: 7%, $C_{18}$: 17%) was prepared by oligomerizing propylene. 130 g of maleic anhydride was added to 300 g of the oligomer by an ordinary method to obtain 213 g of maleic modified reaction product.

COMPARATIVE EXAMPLE 5

An oligomer having 16 to 20 carbon atoms ($C_{16}$: 63%, $C_{18}$: 7%, $C_{20}$: 30%) was prepared by oligomerizing isobutylene. 120 g of maleic anhydride was added to 300 g of the oligomer by an ordinary method to obtain 172 g of maleic modified reaction product.

EVALUATION OF SIZING AGENTS

With regard to the alkenylsuccinic anhydrides that are prepared in Examples 1 to 7 and Comparative Examples 1 to 5, the performance was compared according to the following use method.

USE EXAMPLE 1

To 1 g of alkenylsuccinic anhydride (ASA) were added 20 g of 10% cationized starch and 79 g of water and they were emulsified by a homogenizer. Then, 0.1, 0.2 and 0.5 wt. % (as ASA solid content relative to pulp) mixtures were prepared by adding the obtained emulsion to 1% pulp slurry (L-BKP: laubholz bleached kraft pulp, 450 ml in Canadian standard freeness). With using the prepared pulp slurry and 20% (relative to pulp) of $CaCO_3$, paper of 60±1 g/m² in basis weight was made by a TAPPI standard machine. After dehydration of wet paper by compression, it was dried at 100° C. for 1 minute. The moisture content of the paper was adjusted by putting it into an atmosphere of 65% R.

H. for 24 hours. The properties were then determined by Stöchigt method, the results of which are shown in the following Table 1.

As will be understood from the results in Table 1, the sizing degrees of sizing agents of the present invention are higher than those of Comparative Examples.

TABLE 1

| Test Item | Stochigt Sizing Degree (sec.) | | |
|---|---|---|---|
| Sizing Medium | 0.1% | 0.2% | 0.5% |
| Example 1 | 6 | 12 | 25 |
| Example 2 | 9 | 19 | 32 |
| Example 3 | 7 | 15 | 28 |
| Example 4 | 8 | 16 | 28 |
| Example 5 | 7 | 15 | 27 |
| Example 6 | 7 | 15 | 29 |
| Example 7 | 5 | 10 | 28 |
| Comparative Example 1 | 0 | 0 | 12 |
| Comparative Example 2 | 0 | 7 | 19 |
| Comparative Example 3 | 0 | 8 | 19 |
| Comparative Example 4 | 0 | 7 | 20 |
| Comparative Example 5 | 0 | 0 | 10 |

USE EXAMPLE 2

To 10 g of alkenylsuccinic anhydride was added an emulsifying agent of 1 g of acetylated product of polyethylene glycol nonylphenyl ether (trademark: Noigen EA 160, made by Daiichi Kogyo Seiyaku Co., Ltd.) and they were sufficiently mixed together. 99 g of water was added to 1 g of the above mixture and a sizing medium was prepared by shaking it lightly to emulsify.

To 1% pulp slurry was added a fixing agent of 0.3% (relative to pulp) of polyamide polyamine resin (trademark: AF-100, made by Arakawa Kagaku Kogyo K.K.) and 0.1, 0.2 and 0.5% wt. % (as solid relative to pulp) of the foregoing sizing medium was added to the pulp slurry. Then, in the like manner as Use Example 1, sizing degrees were determined. Furthermore, the prepared dilute sizing medium was left to stand for 24 hours and sizing degrees of 0.5% addition were also determined. These results are shown in the following Table 2.

As will be understood from the results in Table 2, the self-emulsifying sizing agents of the present invention gave excellent sizing degrees just after the preparation as compared with those of Comparative Examples. In addition, lowering of the sizing degrees after 24 hours in this invention was little.

TABLE 2

| Test Item | Stochigt Sizing Degree (sec.) | | | |
|---|---|---|---|---|
| | Just after Emulsifying | | | After 24 Hours |
| Sizing Medium | 0.1% | 0.2% | 0.5% | 0.5% |
| Example 1 | 9 | 15 | 26 | 20 |
| Example 4 | 10 | 19 | 28 | 21 |
| Example 5 | 9 | 18 | 27 | 21 |
| Example 7 | 4 | 13 | 25 | 10 |
| Comparative Example 2 | 0 | 10 | 21 | 3 |
| Comparative Example 3 | 0 | 8 | 21 | 0 |
| Comparative Example 4 | 0 | 9 | 20 | 3 |

USE EXAMPLE 3 To 10 g of the alkenylsuccinic anhydride that was obtained in Example 4, was added 1 g of emulsifying agent shown in the following Table 3 and they were mixed together. The mixture was treated in the like manner as Use Example 2 and sizing degree was determined. Each result is shown in Table 3.

TABLE 3

| ASA | Emulsifying Agent | Stochigt Sizing Degree (sec.) | | | |
|---|---|---|---|---|---|
| | | Just after Emulsifying | | | After 24 Hours |
| | | 0.1% | 0.2% | 0.5% | 0.5% |
| Alkenyl- | 1 | 10 | 19 | 28 | 21 |
| succinic | 2 | 9 | 20 | 27 | 20 |
| Anhydride | 3 | 8 | 19 | 28 | 21 |
| in Example 4 | 4 | 10 | 19 | 27 | 20 |

Notes:
Emulsifying Agents
1: Acetylated product of Noigen EA-160(*)(polyethylene glycol nonylphenyl ether)
2: Acetylated product of Noigen ET-102(*)(polyethylene glycol lauryl ether)
3: Acetylated product of Sorgen TW-20(*)(polyoxyethylene sorbitan monolaurate)
4: Acetylated product of Noigen ES-160(*)(polyethylene glycol monooleate)
(*): Trademark, made by Daiichi Kogyo Seiyaku Co., Ltd.

What is claimed is:

1. A method of sizing paper comprising adding to a pulp slurry a paper sizing agent containing a reaction product and/or a hydrogenation product of said reaction product, said reaction product being prepared by adding maleic anhydride to branched internal olefins having 14 to 36 carbon atoms which branched internal olefins are obtained by oligomerizing one member or a mixture of two or more members of a class of other olefins having 6 to 18 carbon atoms in the presence of an acid catalyst.

2. The method according to claim 1, wherein said other olefins have 8 to 12 carbon atoms.

3. The method according to claim 1, wherein said other olefins are straight chain α-olefins.

4. The method according to claim 1, wherein said other olefins are straight chain internal olefins.

5. The method according to claim 1, wherein the catalyst used for said oligomerization is one member of acid catalysts including cation exchange resin containing fluorosulfonic radicals, synthetic silica-alumina and boron fluoride-diethyl ether complex.

6. The method according to claim 1, wherein said branched internal olefins are those each having a double bond at 3-position or a higher position of main carbon chain and contain 50% or more of olefins which have alkyl branches joined to one or both the carbon atoms of said double bond.

7. The method according to claim 1, wherein said paper sizing agent further contains a dispersing agent.

8. The method according to claim 7, wherein said dispersing agent is one member selected from the group consisting of cationized starch, gelatin, polyvinyl alcohol, cationic polyacrylamide and polyethylene imine.

9. The method according to claim 1, wherein said paper sizing agent further contains an emulsifying agent.

10. The method according to claim 9, wherein said emulsifying agent is one member selected from the group consisting of polyoxyethylene sorbitan fatty acid ester, polyoxyethylene alkyl ether, polyoxyethylene alkyl phenol and polyoxyethylene alkyl ester, and their acetylated products.

* * * * *